(12) United States Patent
Joshi

(10) Patent No.: US 6,617,861 B1
(45) Date of Patent: Sep. 9, 2003

(54) APPARATUS AND METHOD FOR MEASURING AND MONITORING COMPLEXPERMITTIVITY OF MATERIALS

(75) Inventor: Kalpana Joshi, Maharashtra (IN)

(73) Assignee: National Research Development Corporation, New Delhi (IN)

( * ) Notice: Subject to any disclaimer, the term of this patent is extended or adjusted under 35 U.S.C. 154(b) by 0 days.

(21) Appl. No.: 09/717,309

(22) Filed: Nov. 22, 2000

(51) Int. Cl.[7] .................................................. G01R 27/04
(52) U.S. Cl. ...................................................... 324/637
(58) Field of Search ................................ 324/629, 633, 324/635, 636, 637, 643; 333/219, 219.1, 227, 230, 231, 235

(56) References Cited

U.S. PATENT DOCUMENTS

| | | | |
|---|---|---|---|
| 3,510,764 A | | 5/1970 | Heath .......................... 324/633 |
| 3,942,107 A | | 3/1976 | Gerhard ...................... 324/633 |
| 4,829,233 A | | 5/1989 | Flemming et al. .......... 324/637 |
| 5,334,941 A | * | 8/1994 | King ........................... 324/637 |
| 5,686,841 A | | 11/1997 | Stolarcxzyk et al. ........ 324/635 |
| 5,721,194 A | * | 2/1998 | Yandrofski et al. ......... 505/210 |
| 5,744,970 A | * | 4/1998 | Kim et al. ................... 324/636 |
| 5,965,494 A | * | 10/1999 | Terashima et al. .......... 505/210 |
| 6,204,670 B1 | * | 3/2001 | Joshi ........................... 324/643 |

* cited by examiner

Primary Examiner—Safet Metjahic
Assistant Examiner—Etienne LeRoux
(74) Attorney, Agent, or Firm—Venable LLP; George H. Spencer; Catherine M. Voorhees

(57) ABSTRACT

A highly accurate instantaneous numerical analysis software assists on on-line and nondestructive in situ measurement method and instrument for the measurement of complex permittivity of materials in solid, semisolid, granular, sheet, thin and thick films, as well as materials in the liquid state. Such materials may include ceramics, polymer, semiconductor, or dielectric materials used in a circuit board and integrated Circuit manufacturing materials. The measuring instrument is a near field, non-contract apparatus in the form of one from the group of microstrip, coplanar waveguide and asymmetric inhomogeneous stripline. The frequency range may be 50 MHz onwards. The instrument includes a sweep oscillator, a resonator, a detector, a power meter to measure transmitted power with respect to the input signal frequency, a computer and an interface device. The instrument and method works on the basis of analysis of electromagnetic equations along with the measurement of Q factor and shift in the frequency of resonance due to the presence of material under test in the known vicinity of the resonation.

11 Claims, 5 Drawing Sheets

APPARATUS AND METHOD FOR MEASURING AND MONITORING COMPLEXPERMITTIVITY OF MATERIALS

FIELD OF INVENTION

This invention relates to an apparatus and method for measuring and monitoring complex permittivity of materials.

BACKGROUND OF THE INVENTION

Microstrip and microstrip type resonators described are efficient devices for measuring complex permittivity of materials at microwave frequencies as disclosed by Flemming U.S. Pat. No. 4,829,233; by Heath U.S. Pat. No. 3,510,764; and by Gerhard U.S. Pat. No. 3,942,107 and by King U.S. Pat. No. 5,334,941. Flemming describes a method in which a resonator is mounted or the copper-backed substrate. A resonator is weakly coupled to a microwave feed source and to a microwave detector so that the resonator Q factor is unaffected by the impendances of the source or the detector. When the test dielectric is placed near the resonator, the electromagnetic fields near the resonator are coupled to the material under test so as to affect the resonator frequency of resonance, as well as Q factor.

The resonator frequency and Q factor measurements are done in the transmission mode. Further the methods for modulating source or resonant frequency are disclosed which avoids the need for the swept source.

Heath uses a half wavelength microstrip resonator, which is tightly sandwiched between two sheets of sample test material. These sheets of sample material are clamped in a special fixture. The microstrip resonator is loosely capacitively coupled to the microstrip feed line, which passes near one end of the resonator normal to the resonator length. The dielectric constant is determined from the measurement of resonant frequency and Q factor for the transmission between sensor's two input and output ports. As the special cutting and positioning of thin sheets of the sample material is required; Heath's method is not in situ or non-destructive.

King relates to the use of a microwave reflection resonator sensor for complex permittivity measurement in situ. The microstrip resonator is fed from the ground plane side through a slot.

Microwave power is coupled to the slot through a coaxial line or a microstrip. The material under test is kept in contact with the sensor. The resonant frequency and input power coupling factor is measured at the resonant frequency. The real and imaginary parts of permittivity ($\in'$ and $\in''$) or the conductivity ($\sigma$) are determined from the resonant frequency and coupling coefficient data using approximate closed form expressions. King uses bottom fed resonators which King claims to be a major modification but this leads to complicated assembly and unstable mounting compared to the side-coupled resonator. The approximation in the basic expression of capacitance of the cross section of the sensor leads to the serious inaccuracies in the results. The closed form expressions need to use standards for calibration to evaluate constants. King depends upon empirical or analytical calibration. Evaluation of the constants before the installation and commissioning of the sensor is essential. The starting equation of effective capacitance of King is based on the assumption that the fringing field constant is the same for all thicknesses of a sample. Our analysis (FIG. 12) shows that the resonant frequency varies with the permittivity, as well as material thickness. King is limited to the measurement of infinitely thick samples only. The empirical calibration techniques of King leads to errors if the thickness of the sample is different than the calibration standard. While King is directed to an in situ sensor, it is not possible to perform in situ calibrations in most situations, as the chamber cannot be filled with the calibration liquid or solid. Therefore, King leads to errors in the calculated and true data due to calibrations using standards. The same is true for the analytical calibrations as the actual surface irregularities and air gaps between the resonator and the solid sample contribute to the errors in measurements. It is essential to validate analytical technique with the standard data. Dispersion in microstrip with dielectric overlay also plays an important part in errors. None of the empirical calibration techniques using closed form expressions account for dispersion. The shifts in the resonant frequency can be larger than 1 GHz at the material permittivities of 10 (FIG. 13). Hence, dispersion affects accuracy at the first decimal place of permittivity. Both Flemming and Heath involve transmission from one input port to an output port. Both ports are loosely and capacitively coupled to the intervening resonator by capacitive coupling. King relates only to the critically coupled reflection one port sensor. King relates to samples of very large size compared to the sensor. Gerhard relates to the measurement real part of the dielectric constant only. The samples under consideration are thin sheets of dielectric materials.

Gabelich measures dielectric homogeneity at 100 KHz to 2 MHz for the use of dielectric substrates for CTS-ESA radar antennas on Barium STrontium Titanate (BST). The C band or microwave permittivity is co-related to low frequency permittivity even though it is not accurate enough. Further, Gabelich measures only the real part of permittivity.

U.S. Pat. No. 5,686,841 Nov. 11, 1997, Stolarczyk et. al teach the use of patch antenna to detect presence of ice, water and/or antifreeze mixtures on wings of the aircraft or roads. A single frequency is fed to the antenna which is one of the arms of the bridge circuit. This frequency is varied until admittance of the antenna approaches zero. The object of the Stolarczyk's invention is not to accurately determine complex or real permittivity but to only detect formation of ice. The frequency resolution of the frequency variation is very low, of the order of 2.4 MHz.

SUMMARY OF THE INVENTION

A primary object of this invention is to propose a process and apparatus for the measurement and monitoring of complex permittivity and conductivity of materials in situ which is accurate.

Another object of this invention is to propose a process and apparatus for the measurement and monitoring of complex permittivity and conductivity of materials in situ using automatic scalar or vector network analyzers or swept frequency generators and peak detectors that perform fast and accurate frequency and amplitude measurements.

Still another object of this invention is to propose a process and apparatus for the measurement and monitoring of complex permittivity and conductivity of materials in situ employing online numerical analysis software performing numerous iterations to arrive at convergence within few seconds with required accuracy like ±0.1 or ±0.01 in case of $\in$ and ±0.0001 or ±0.0005 in case of $\in$.

Yet another object of this invention is to propose a process and apparatus for the measurement and monitoring of complex permittivity and conductivity of materials in situ and wherein the determination of real and imaginary parts of permittivity takes place in a relatively short period.

A further object of this invention is to propose a process and apparatus for the measurement and monitoring of complex permittivity and conductivity of materials in situ and wherein the permittivity measurement does not depend on the first order approximations and simplistic closed form expressions involving unknown constants.

A still further object of this invention is to propose a process and apparatus for the measurement and monitoring of complex permittivity and conductivity of materials in situ where the materials used may be one of high frequency circuits boards, various bulk polymers and semiconductor materials.

Yet a further object of this invention is to propose a process and apparatus for the measurement and monitoring of complex permittivity and conductivity of materials in situ and wherein transmission type resonators may be used for samples of smaller size than the resonator.

The invention provides a device and process for measuring and monitoring complex permittivity of materials for quality control, in situ and in the materials measurement laboratory. Material under test is kept as an overlay on a microstrip, asymmetric stripline, co-planar waveguide, patch or a disc resonator. The resonator has its resonant frequency in the range of 0.5 to 20 GHz. The material is placed in contact with the top conductors of the circuits or with a finite air gap above the top conductor. The ground plane at the top may or may not be used. A fringing field from the top surface and the edges of the resonator passes through the material under test, which is kept as an overlay dielectric. As the fields above the substrate pass through the material under test the effective permittivity of the resonator increases. The Q factor ($Q=\beta/2\alpha$) of the resonator changes due to a change in the propagation constant ($\beta$) and attenuation constant ($\alpha$). An increase in the effective permittivity of a microstrip, asymmetric stripline, coplanar waveguide resonator, rejection filter, patch or a disc causes a decrease in the resonant frequency of the resonator. That is, the Q factor of the resonator decreases as the attenuation due to overlay adds to the total losses.

The invention envisages the use of transmission as well as reflection type resonators. The resonators are coupled to the source of microwave power using direct or gap coupling (capacitively or inductively) from the side of the microstrip conductor and not from the ground plane side. The measurements may be one port or two port depending upon the dimensions of the material under test. If a swept frequency source is used then a resonant dip may be observed in the reflection or transmission mode with the available instrument accuracy. The Q factor is directly measured using half power frequencies and the resonant frequency. The unloaded Q measurement is preferred for the accurate measurement $\in$" or $\sigma$. If a loaded Q is measured, then it is necessary to calculate an unloaded Q from the loaded Q factor. The resonant or half power frequencies may be automatically or manually measured and fed to the computer using a data acquisition system and/or frequency tracking device. The dedicated computer program calculates real and imaginary parts of the complex permittivity or conductivity of the material under test. The program is based on the numerical analysis of a microstrip embedded in multiple dielectric layers, the material under test being the layer of unknown permittivity.

BRIEF DESCRIPTION OF THE DRAWINGS

The invention will be further described with the help of accompanying drawings, in which.

DETAILED DESCRIPTION OF THE INVENTION

Figure 1:
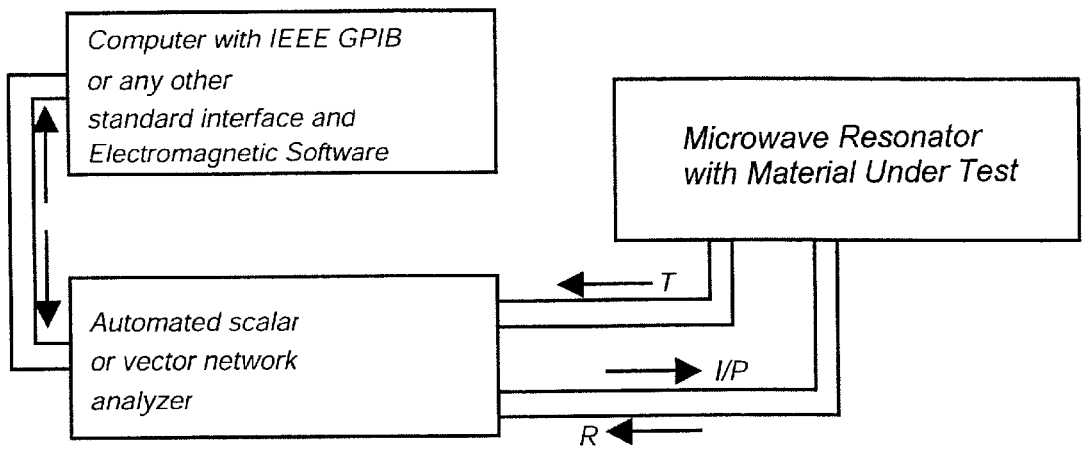
FIG. 1 shows a block diagram of an instrument using a scalar or vector Network analyzer.
Figure 2:
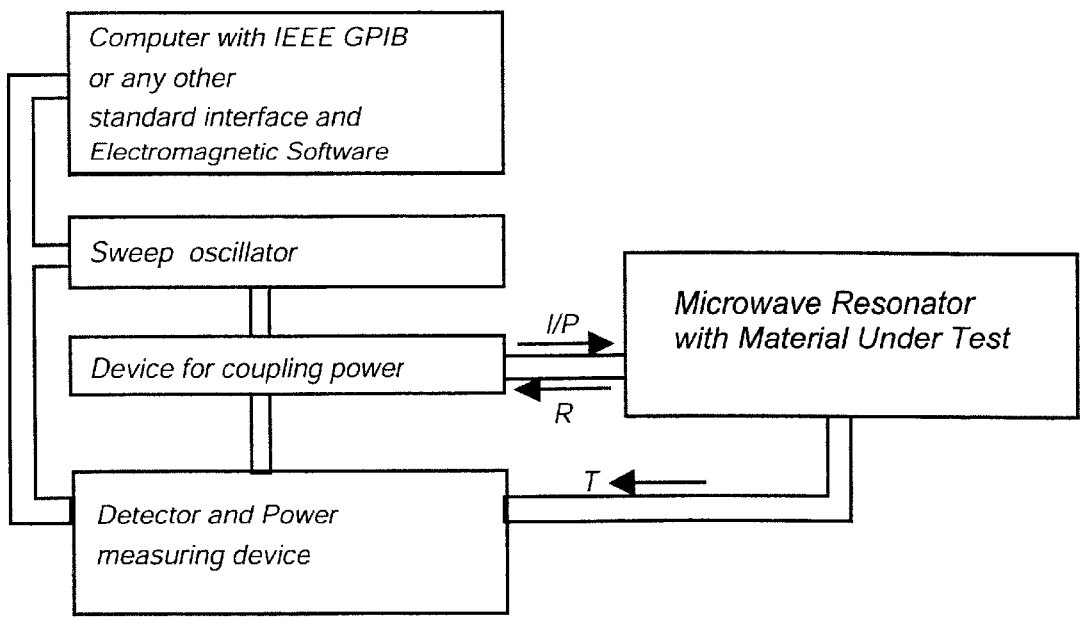
FIG. 2 shows a diagram of an instrument using a detector and power measuring device.

With reference to the drawings, FIGS. 1 and 2 are schematic diagrams showning an arrangement of the apparatus for the use in this invention. FIG. 1 shows an instrument for the determination of complex permittivity of materials comprising:

I. Automated scalar or vector network analyzer; II. reflection or transmission type microwave sensors of any type and as shown in FIGS. 3, 4, 5, 6, 7, 8, 9, 10, 11; III. A computer with IEEE GPIB or any other standard interface; IV. Data acquisition and postprocessing numerical analysis software for the determination of complex permittivity loaded on the computer.

FIG. 2 shows a schematic diagram of the instrument using I. a sweep generator; II. a reflectometer bridge or directional coupler; III. a power meter or Voltage Standing Wave Ratio (VSWR) meter; IV. Computer with IEEE GPIB or any other standard interface; and V. a reflection or transmission type microwave sensor 2 or 7 of any type shown in FIGS. 3, 4, 5, 6, 7, 8, 9, 10, and 11. The network analyzer has a built in synthesized sweep generator which generates swept frequency output with the required frequency span. The frequency resolution of the sweep generator can be as high as 1 Hz. The output power level may be adjusted to the required value. The swept microwave power output of the sweep generator is coupled to the sensor circuit via a special purpose test fixture and a coaxial cable. If the sensor in the test fixture is of reflection type then a directional coupler or a reflectometer bridge is used to isolate reflected power and then it is coupled to the detector port. The reference signal is being fed externally in case of a scaler network analyzer. The network analyzer calculates the ratio of reflection and/or transmitted parameters to the input power to the sensor for the range of swept frequencies. The resonant frequency is displayed on the screen as a sharp peak and is observed due to the storage of power in the resonator. The half power frequencies are observed on the screen with the help of a 3 dB search, which may be automatic or manual. According to the block diagram of FIG. 2, the sweep generator generates a swept signal and is fed to the sensor 2 or 7 through the reflectometer bridge. The test specimen 4 of unknown permittivity is kept as an overlay on the reflection sensor. Microwave power is coupled to the reflection sensor 2 or 7 through a coaxial cable using a standard coaxial to microstrip transition, like a SMA connector. The reflectometer separates the reflected signal from the outgoing signal and is measured by the power meter. The transmitted signal can be measured by the power meter directly. The resonance is detected by the displayed power output reading of the sensor at the particular frequency. The frequency resolution of the instrument and process is the resolution of the sweep generator which can be as high as 1 Hz.

Figure 3:
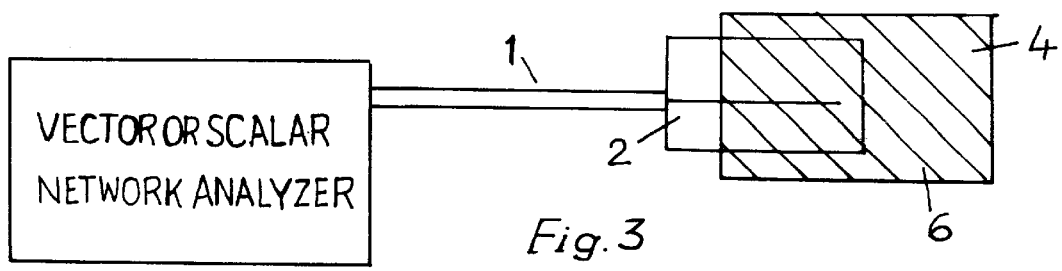
FIG. 3 shows a block diagram of an instrument with a reflection type sensor and the test specimen.

FIG. 3 shows a block diagram with an automated scaler or vector network analyzer, coaxial cable 1, reflection type microwave sensor 2, test specimen 4 of unknown permittivity 6 kept as an overlay on the reflection sensor.

Figure 4:
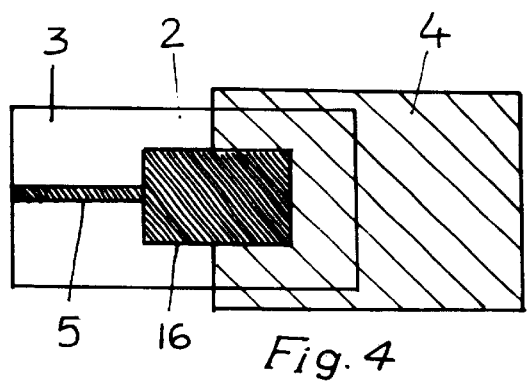
FIG. 4 shows a schematic diagram of a direct coupled, reflection type sensor (microstrip patch antenna) and the test specimen.

FIG. 4 shows a schematic diagram of a microstrip patch antenna 16 as a reflection sensor 2 delineated on substrate 3 of known permittivity ∈1, with the feed line 5 and the test material 4 kept as an overlay.

Figure 5:
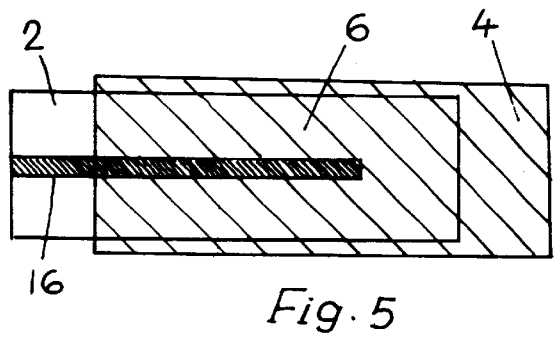
FIG. 5 shows a schematic diagram of a direct coupled, reflection type microstrip sensor (quarter or half wavelength) and the test specimen.

FIG. 5 shows a schematic diagram of a microstrip quarter or half wavelength resonator as a reflection sensor 2 delineated on substrate 3 of known permittivity ∈1, with the feed line 5 and the test material 4 of the unknown permittivity 6(∈) kept as an overlay.

Figure 6:
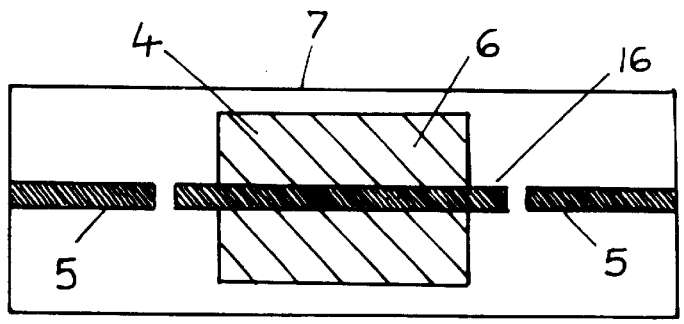
FIG. 6 shows a schematic diagram of a gap coupled, transmission and/or reflection type sensor (quarter or half wavelength) and the test specimen.

FIG. 6 shows a schematic diagram of a gap coupled half wavelength microstrip resonator as a transmission sensor 7 with the feed line 5 and the test material 4 of unknown permittivity ∈ kept as an overlay.

Figure 7:
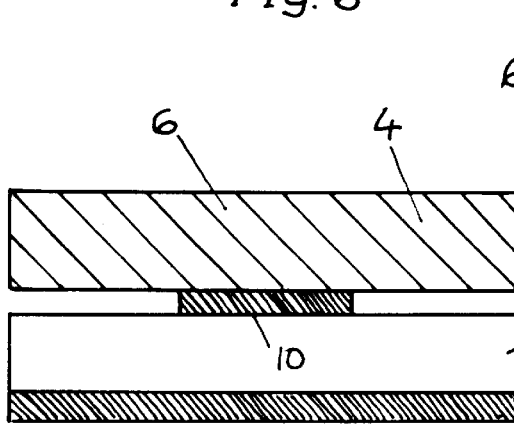
FIG. 7. shows a cross sectional diagram of a transmission and/or reflection type microstrip sensor and the test specimen of finite height.

FIG. 7 shows a cross sectional diagram of a microstrip sensor conductor 10, ground plane 9, substrate 8 and the test specimen 4 of finite height and unknown permittivity 6(∈) kept as an overlay.

Figure 8:
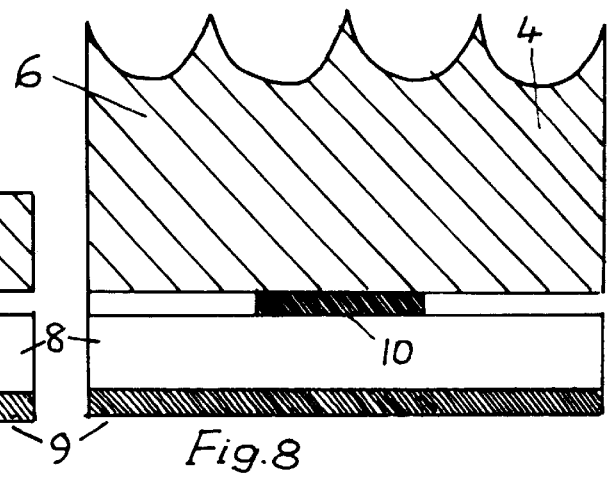
FIG. 8 shows a cross sectional diagram of a transmission and/or reflection type microstrip sensor and bulk test specimen with very large dimensions.

FIG. 8 shows a cross sectional diagram of a microstrip sensor conductor 10, ground plane 9, substrate 8 and the test specimen 4 of finite height and unknown permittivity 6(∈) kept as an overlay. The bulk test specimen 4 is shown to be of very large dimensions.

Figure 9:
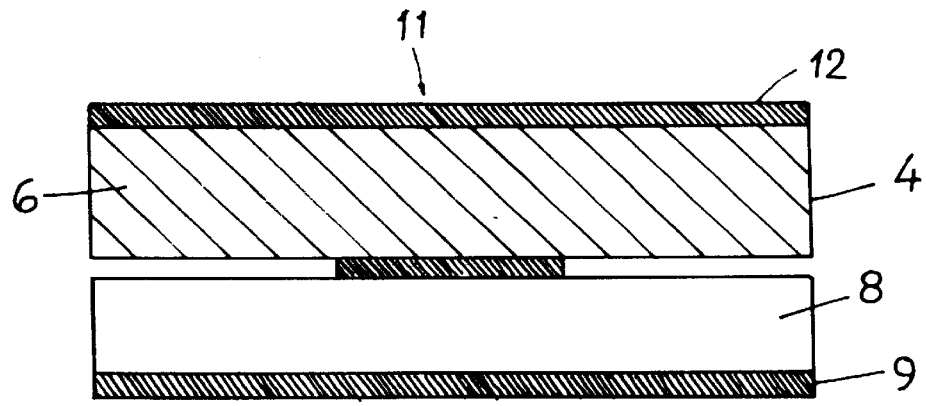
FIG. 9 shows a cross sectional diagram of a transmission and/or reflection type asymmetric stripline sensor and test specimen of finite height.

FIG. 9 shows a cross sectional diagram of a transmission and/or reflection type asymmetric stripline sensor 11, with a microstrip sensor conductor 10, ground plane 9, substrate 8 and the test specimen 4 of finite height and unknown permittivity 6(∈) kept as an overlay and a top ground plane 12.

Figure 10:
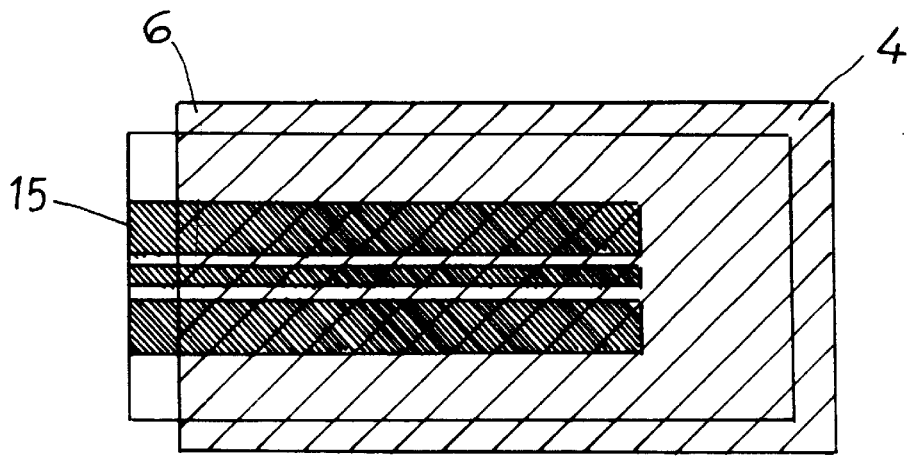
FIG. 10 shows a schematic diagram of a direct coupled, reflection type coplanar waveguide sensor (quarter or half wavelength) and the test specimen.

FIG. 10 shows a schematic diagram of a direct coupled, reflection type coplanar waveguide sensor 15 (quarter or half wavelength) and the test specimen 4 unknown permittivity 6(∈) kept as an overlay.

Figure 11:
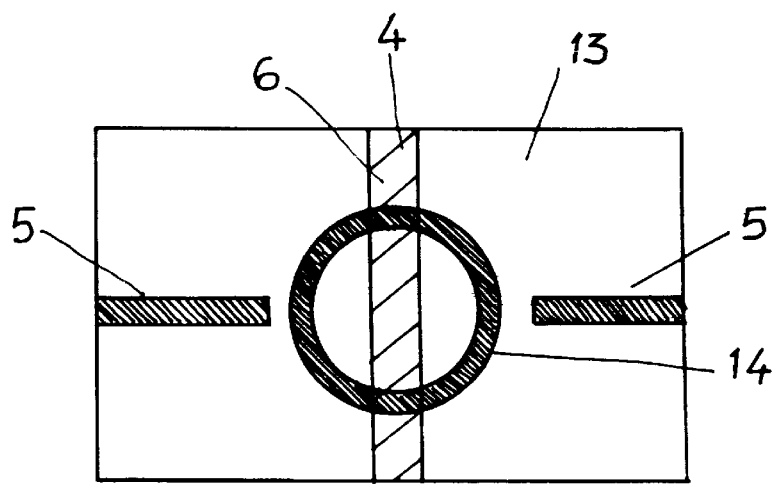
FIG. 11 shows a schematic diagram of a gap coupled, transmission type microstrip ring resonator sensor (one wavelength) and the test specimen.

FIG. 11 shows a schematic diagram of a gap coupled, transmission type microstrip ring resonator sensor 14 (one wavelength) and the test specimen 4 of smaller dimensions than the resonator length having unknown permittivity 6(∈) kept as an overlay at the 90 orientation with respect to the feed line 5.

Figure 12:
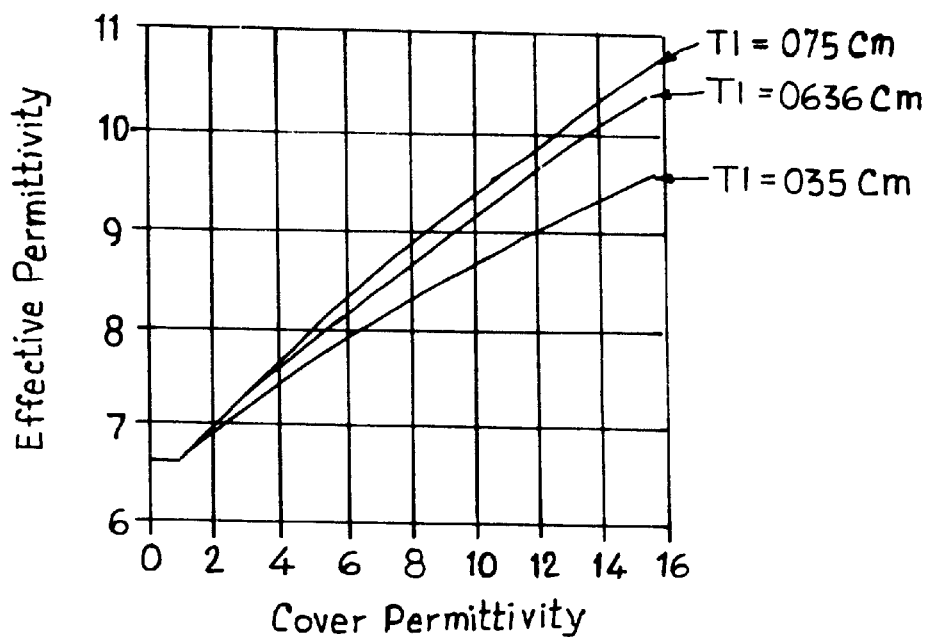
FIG. 12 is a graph showing the variation of effective permittivity with respect to cover permittivity of a test material.

FIG. 12 shows results of the numerical software of the present invention simulating a reflection or transmission type microstrip sensor. The graph shows the variation of effective permittivity with respect to cover permittivity and test material thickness when the test material completely overlaps the sensor. This graph indicates the difference between other inventions using microstrip resonator sensors kept in the vicinity of test material. This invention does not use any approximate closed form expressions for the calibration of sensor but uses an on-line numerical analysis which does not require use of known standards or empirical calibrations (like Flemming et al. U.S. Pat. No. 4,829,233 or King U.S. Pat. No. 5,334,941). That is, the instant invention uses on-line or off-line computer software.

Figure 13:
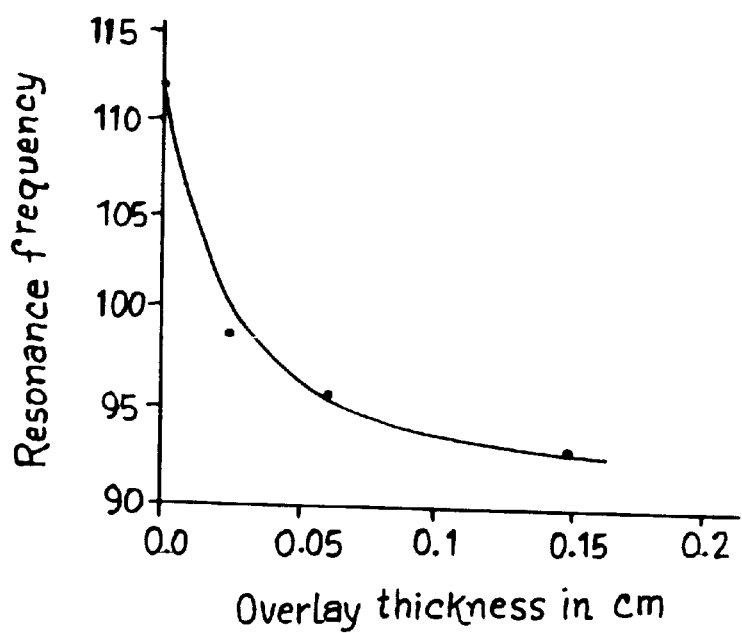
FIG. 13 is a graph with the resonance frequency on the ordinate and the overlay thickness on the abscissa.

FIG. 13 shows a comparison of experimental data with the simulation of frequency shift of 99.99% pure alumina kept as a overlay on a microstrip resonator.

Figure 14:
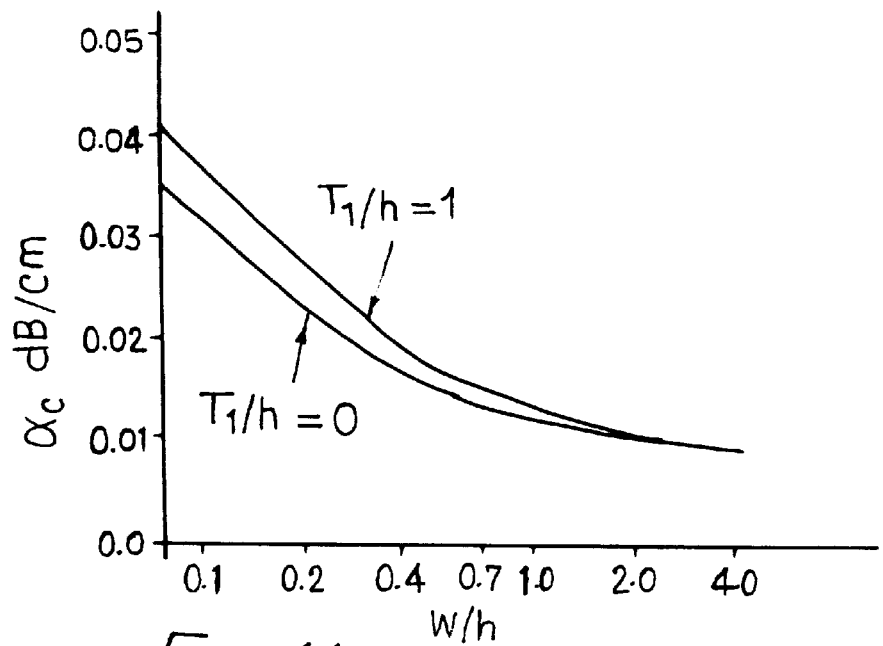
FIG. 14 shows a simulation of a conductor attenuation.

FIG. 14 shows a simulation of a conductor attentuation with 99.99% pure alumina as a substrate and overlay on a microstrip resonator, where T is an overlay thickness and h is the substrate height.

Figure 15:
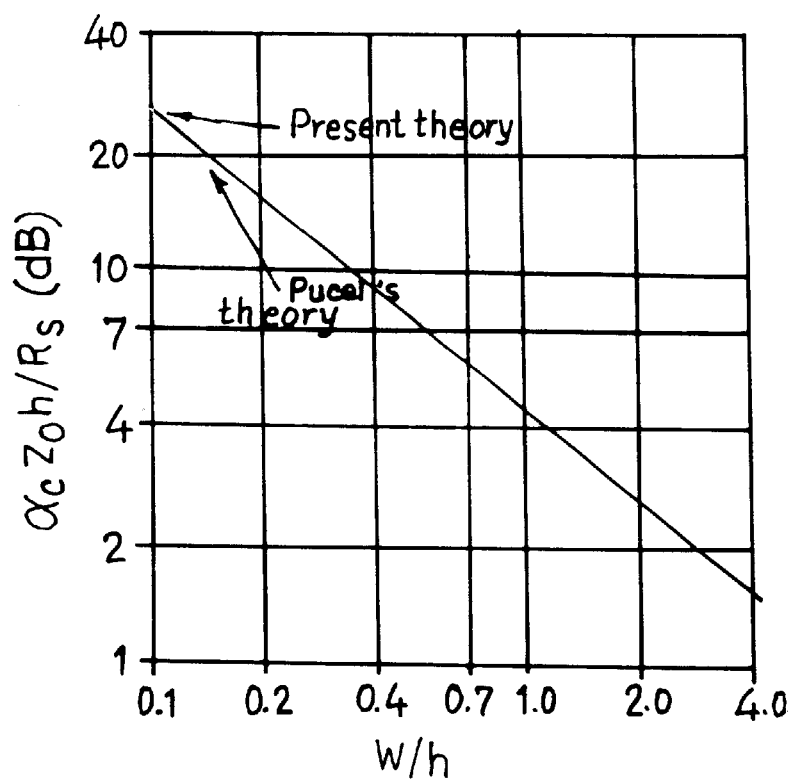
FIG. 15 shows the comparison of conductor attentuation.

FIG. 15 shows the comparison of the simulation of conductor attentuation with Pucel's theory for an open microstrip, where h is the substrate height.

An on-line computer with data acquisition software and hardware is optional. Resonant and half power frequency data from microwave test setup is manually fed to the computer through the interactive user friendly software for the post-processing of data and determination of complex permittivity of specimen under test. A dedicated computer program computes complex permittivity using electromagnetic numerical analysis software analyzing resonator embedded (FIGS. 7, 8) in multiple dielectric layers. The program takes less than three seconds on the IBM compatible computer with Pentium 350 $MH_z$ processor and three minutes on 80386 processor. The user can choose the required accuracy.

The material under test, 4 for which complex permittivity, 6 is to be measured is kept in direct contact of the resonator or keeping a gap of few microns from the resonator. A top ground plane, 12 is optional. The computer program needs to be fed the information on the type of resonator configuration as well as presence of top ground plane and thickness and length of the material under test. The test set up needs to be calibrated for acceptable connector assembly. The resonator is tested without the presence of material under test initially. The resonant frequency and half power frequency are measured and fed to the program. The sample or material under test, 4 is then placed over the resonator in the required orientation and the specified position. The sensor is placed in the reaction chamber or a drier or in the moving belt in case of flowing material without disturbing the connector assembly. The presence of dielectric material in the vicinity of the resonator shifts frequency of resonance due to the increase in the effective permittivity, $\in_{eff}$ of the resonator.

$$f_s/f_o = (\in_{effo}/\in_{effs})^{0.5} \qquad (1)$$

Where subscripts "o" and "s" stand for open and with loaded sample.

At resonance electrical length of a microstrip resonator is an integral multiple of half wavelengths. The real part of effective permittivity ($\in_{\mathit{eff}}$) of an open resonator is determined by the software program by feeding width of the top conductor, substrate permittivity, substrate loss tangent and substrate permittivity. It is necessary to know these values most accurately as the errors and uncertainties in these values will reflect on the resultant values of permittivities of specimens kept as overlays. Hence utmost care is required in designing and fabricating the test vehicle. The $\in_{\mathit{effs}}$ thus determined is numerically postprocessed by the program to determine specimen real part of the permittivity $\in'_r$; the required accuracy may be fed to the interactive program at the maximum of ±0.01.

The Quality factor, Q of the resonator changes due to the additional dielectric and conductor losses due to the overlay material. Our numerical analysis shows an increase in the total loss due to dielectric cover (FIG. 15). The unloaded Q factor of a resonator is given by the standard equation:

$$Q_{total} = \beta/2\alpha \qquad (2)$$

Where $$\alpha_{total} = \alpha_{conductor} + \alpha_{dielectric} + \alpha_{radiation} \qquad (3)$$

where β is a propagation constant and $$Q_{total} = Q_{unloaded}.$$

The software also calculates conductor loss for the microstrip with cover specimen. This is not same as an open microstrip conductor loss[7]. The program evaluates the dissipation factor of cover specimen from the given data using electromagnetic numerical analysis. The radiation loss can be neglected if desired.

$$\alpha_{total} - \alpha_{conductor} = \alpha_{dielectric}\ \alpha_{radiation} \qquad (4)$$

Neglecting radiation losses the program calculates contribution of cover dielectric to the dielectric loss and hence gives the value of dissipation factor or loss tangent (tan) of the sample $$1/Q_{total} = 1/Q_c + 1/Q_d + 1/Q_r \qquad (5)$$

where $Q_c$=Quality factor due to conductor losses
$Q_d$=Quality factor due to dielectric losses
$Q_r$=Quality factor due to radiation losses
Let $Q_t$(open)=Total Quality factor of an open microstrip resonator
$Q_t$(cover)=Total Quality factor of a covered microstrip resonator
$\alpha_t$(open)=Total attenuation per unit length of an open microstrip resonator
$\alpha_t$(cover)=Total attenuation per unit length of a covered microstrip resonator $$\alpha_{t(cover)} = \alpha_{c(cover)} + \alpha_{d(open)} + \alpha_{d(cover)} + \alpha_{r(cover)} \qquad (6)$$

The numerical analysis indicates conductor loss $\alpha_{c(cover)}$ as well as $\alpha_d$ of a microstrip with dielectric cover is larger than the open microstrip. For low permittivity and lossy materials the increase in the conductor loss may be neglected $$1/Q_{t(cover)} - 1/Q_{t(open)} = 1/Q_{d(cover)} \qquad (7)$$

Neglecting radiation losses.

$$d = [27.3/(\lambda_0 \in_{\mathit{effs}})][q_1 \in_1 \tan \delta_{(substrate)} + q_{2\ 2} \tan \delta_{(cover)}] \qquad (8)$$

where
$q_1$=filling fraction due to substrate
$\in_1$=real part of permittivity of substrate
$q_2$=filling fraction due to dielectric cover
$\in_2$=real part of permittivity of the cover $$\alpha_{d(cover)} = [27.3/(\lambda_0 \in_{\mathit{effs}})][q_2 \in_2 \tan \delta_{(cover)}] \qquad (9)$$

It can be noticed that determination of $\in''$ or tan δ requires a value of $\in'$ of the test material. King (U.S. Pat. No. 5,334,941) neglects dependence of $\in'$ on the effective capacitance and treats effective capacitance as a constant, which is certainly not the case. Therefore determination of $\in''$ has inherent inaccuracy in King's method.

This invention actually used a highly accurate value of $\in'$ in the determination of $\in''$ along with the numerically calculated conductor and dielectric losses.

$$1/Q_{d(cover)} = \pi/\alpha_{d(cover)} \lambda g \qquad (10)$$

$$\alpha_{d(cover)} = \pi Q_s \lambda g \qquad (11)$$

From equations (9) and (11)

$$\tan \delta_{(cover)} = \pi Q_s (\in_{\mathit{effs}})^{1.5}/27.3 q_2 \in_2 \qquad (12)$$

where the program uses the value of $_2$ obtained numerically beforehand and $$q^2 = (\in_{\mathit{effs}} - \in_{\mathit{effo}})/(\in_1 - 1) \qquad (13)$$

In case materials with very low values of tan δ increase in the conductor loss due to increased effective permittivity needs to be subtracted from the total loss. The computer program takes care of it from the determined value of tan δ. Hence the process is applicable to materials with high and low loss dielectrics including materials used for high frequency applications in microwave region.

Measurement of Material Samples That are Smaller in Dimensions than That of the Resonator The invention provides a process of measurement of complex permittivity of samples that are smaller in length (FIG. 6) and breadth (FIG. 11) than that of the resonator. The examples of such samples are a single grain of wheat, coffee, rice, GaAs, diamond and other precious stones, various types of medicine capsules etc. The invention can be used for studying sample to sample variations in the complex permittivity of objects of the dimensions of few millimeters. The software will ask for the dimensions of the material sample under test and will follow the required subroutine.

For a halfway resonator $$1_1(\in_{\mathit{eff1}})^{0.5} + 1_2(\in_{\mathit{eff2}})^{0.5} = n\lambda_0/2 \qquad (14)$$

where subscripts 1 and 2 stand for different materials overlaying the resonator.

If the sample is partially covering the resonator in the region 2 then $\in_{\mathit{eff1}}$ assumes the value of effective permittivity for the open microstrip and $1_1$ is the length of the open region of the resonator. $\in_{\mathit{eff2}}$ is the unknown value of effective permittivity of the overlaid microstrip at the frequency of operation. Equation holds for both real and imaginary parts of $\in_{\mathit{eff}}$. The effect of dispersion needs to be taken into account. In the present invention software is taking care of dispersion. The unknown effective permittivity is determined using the equation (15) by the software.

It is possible to use this technique at the manufacturing site to monitor chemical reactions involving insulating or low conductivity materials and quality of materials like poly tetra fluro ethylene (PTFE) and other polymer, rubbers and foams. The instrument and the process may be used at the various stages of manufacturing or curing or processing of polymer, organic, food or agricultural products to ensure the final quality. The process and instrument may be used to detect voids, porosity, cracks, and non-uniformity of permittivity or density of the material.

The microstrip resonator used as a test vehicle may be pre-calibrated before the measurement starts. It may also be possible to use calibration standard overlays to define system uncertainties. After establishing acceptable connector assembly the connector and fixture repeatability does not affect sample to sample measurements. This is due to the fact that input and output cables and connections to the resonator and/or test vehicle are tested before the sample is loaded and are unaltered thereafter during measurement. It is not necessary to connect the disconnect the test vehicle if next sample is to be measured. This is a significant circuit boards and materials like IPC-TM-650, no. 2.5.5.5.1, and the document of International Packaging Commission.

The test vehicle design may include care for avoiding loading error so that loading error is avoided with confidence. This is a distinct advantage as the loading error uncertainties remain to be tacked at the time of measurements in method IPC-TM-650, no. 2.5.5.5.1. The loading time for the specimen may be of a few seconds. The response of a network analyzer is within a fraction of a second. Determination of permittivity with the computer takes few seconds. Therefore the measurements may be very fast for multiple samples. The accepted methods require either fabrication of microstrip resonators on the sample under test or need a complicated assembly clamping which may take longer for each sample measurement.

The present invention exploits maximum resolution of frequency source and detector of Network analyzers which is quoted to be 1 $H_z$ by Hewlett Packard for its vector Network analyzers. Patch antenna of either rectangular or disc shaped is used to determine real dielectric constant with the accuracy of +0.015 and tan to the accuracy of +0.0001 or more. Single antenna or any other type of resonator is used to measure complex permittivity with the help of online numerical analysis program.

There are many differences and uses of the present invention in comparison with the inventions of Health, Flemming, Gerhard, Gabelich and King. In particular, a variety of sample dimensions can be accommodated from 3 mm (FIGS. 6, 11) e.g. wheat or rice grain or pallet or tablet; to very large dimensions in length and breadth (FIGS. 4, 5, 8, 10). Depth of the sample may be as small as 0.1 mm (FIGS. 6, 7, 8) to few meters deep (FIGS. 4, 5, 6, 8, 10, 11). The present invention can also be used for the measurement of complex permittivity (FIGS. 7, 8, 10) and dielectric homogeniety in the sheets of dielectric materials. The test material needs to be moved relative to the sensor, or multiple sensors may be employed in the production process. The present invention uses on-line numerical analysis software which has been validated for variety of materials of known permittivities which include ceramic and semiconductor substrates like 99% alumina and semi-insulating GaAs, high frequency circuit board materials like PTFE and wheat grains. The present invention provides on-line or off-line numerial analysis software which gives results of complex permittivity directly from the resonant frequency and Q factor data acquired from the scalar or vector network analyzer or the microwave test equipment. The thickness, length and breadth of the sample need to be fed to the program along with the data on sensor dimensions in the set up routine.

This method of the invention is for in situ or off line measurement of relative permittivity ($\in$) and the dissipation factor or loss tangent (tan δ) of circuit board substrates, ceramic substrates, ceramic and any insulating or low conductivity bulk materials of any thickness under microstrip overlay conditions. Measurements are made by measuring resonance of a length of a planar transmission line of the following types:

1. Microstrip or asymmetric stripline open ended direct coupled resonator;
2. Microstrip or asymmetric stripline gap coupled resonator;
3. Microstrip or asymmetric stripline ring resonator;
4. Microstrip or asymmetric stripline patch antenna;
5. Microstrip or asymmetric stripline rejection filter; and
6. Co-planar waveguide resonators using direct or gap coupling.

The frequency range of measurements may be from 0.5 GHz to 20 GHz. The method under consideration essentially works on the principle of dielectric overlay on a microstrip resonator. The resonant frequency of the resonator under consideration shifts to the lower side due to the increase on the effective permittivity of a test vehicle. The quality factor of the resonator changes due to the changes in the attenuation and propagation constant of the microstrip with dielectric overlay. The method is based on the quasi-static analysis of a microstrip embedded in the multiple dielectric layers. The frequencies with and without dielectric overlay are fed to the computer program along with respective unloaded quality factors. The substrate dimensions, width of the microstrip resonator, thickness of the dielectric under test, kept as an overlay are fed as data to the computer program. The required accuracy can be chosen in the interactive software. The interactive software is based on the principle of analysis of a microstrip embedded in multiple dielectric layers. The software calculates the measured effective permittivity and it searches a suitable overlay permittivity value to find the permittivity of the material under test with the given data of planar transmission line parameters. The dissipation factor or loss tangent (tan δ) is calculated using a unloaded quality factor data with and without sample with the software program.

What is claimed is:

1. An instrument for the measurement of complex permittivity of dielectric materials in solid, liquid and semisolid state comprising:

(a) a microwave resonator selected from the group of transmission and reflection resonators, said microwave resonator having a resonator surface;
   (b) a microwave sweep oscillator, the output of which is coupled to the microwave resonator;
   (c) a detector associated with the microwave resonator for detecting a frequency shift and a Q factor of the microwave resonator;
   (d) means for coupling power to and from the microwave resonator;
   (e) means for measuring the power supplied to and received from the microwave resonator;
   (f) a computer interfaced with a system with components including the microwave sweep oscillator, the microwave resonator, the detector and the means for measuring the power;
   (g) electromagnetic software for the analysis of complex permittivity of the dielectric materials; and
   (h) an interfacing software for communication between components of the system and the computer.

2. The instrument for the measurement of complex permittivity of dielectric materials according to claim 1, wherein the reflection microwave resonator is selected from the group consisting of
   (a) a microstrip ring resonator;
   (b) a microstrip half wavelength resonator;
   (c) a microstrip quarter wavelength resonator;
   (d) a microstrip patch resonator;
   (e) a coplanar wave-guide half wavelength resonator;
   (f) a coplanar wave-guide quarter wavelength resonator;
   (g) an asymmetric stripline half wavelength resonator; and
   (h) an asymmetric stripline quarter wavelength resonator.

3. The instrument for the measurement of complex permittivity of dielectric materials according to claim 1, wherein the transmission type of microwave resonator is selected from the group consisting of:
   (a) a microstrip ring resonator;
   (b) a microstrip half wavelength resonator;
   (c) a coplanar wave-guide half wavelength resonator; and
   (d) an asymmetric stripline half wavelength resonator.

4. The instrument for the measurement of complex permittivity of dielectric materials according to claim 1, wherein the microwave resonator is a non-contact sensor and is attached with a device for loading and unloading the dielectric material under test with a known separation from the resonator surface.

5. The instrument for the measurement of complex permittivity of dielectric materials according to claim 1, wherein the resonator surface is coated with a protective coating selected from the group consisting of a thin film, a thick film and a dielectric sheet.

6. A process for the measurement of complex permittivity of dielectric materials comprising:
   pre-calibrating a measurement system;
   connecting a microwave resonator to the measurement system;
   recording the characteristic response of the microwave resonator;
   determining the resonant frequency, loaded and unloaded quality factor of the microwave resonator;
   determining an effective permittivity of the open microwave resonator, $\in_{effo}$ by using electromagnetic software;
   placing a dielectric material to be tested over the microwave resonator;
   recording the characteristic response of the microwave resonator with the dielectric material under test as an overlay on the microwave resonator;
   determining the resonant frequency, loaded and unloaded quality factor of the resonator with the dielectric overlay; and
   determining an effective permittivity of the microwave resonator with the dielectric overlay, $\in_{effs}$ using the equation $$f_o^2/f_s^2 = \in_{effs}/\in_{effo};$$

and
   determining real and imaginary parts of permittivity ($\in'$ and $\in''$) of the dielectric overlay using the electromagnetic software.

7. The process for the measurement of complex permittivity of dielectric materials according to claim 6 further comprising the step of:
   selecting a reflection resonator, as the microwave resonator, from the group consisting of:
   (a) a microstrip ring resonator;
   (b) a microstrip half wavelength resonator;
   (c) a microstrip quarter wavelength resonator;
   (d) a microstrip patch resonator;
   (e) a coplanar wave-guide half wavelength resonator;
   (f) a coplanar wave-guide quarter wavelength resonator;
   (g) an asymmetric stripline half wavelength resonator; and
   (h) an asymmetric stripline quarter wavelength resonator.

8. The process for the measurement of complex permittivity of dielectric materials according to claim 6 further comprising the step of:
   Selecting a transmission type resonator, as the microwave resonator, from the group consisting of:
   (a) a microstrip ring resonator;
   (b) a microstrip half wavelength resonator;
   (c) a coplanar wave-guide half wavelength resonator; and
   (d) an asymmetric stripline half wavelength resonator.

9. The process for the measurement of complex permittivity of dielectric materials as claimed in claim 6 further comprising the step of:
   loading the dielectric material under test with a known separation from the resonator, said separation being provided with a protective dielectric coating.

10. The process for the measurement of complex permittivity of dielectric materials as claimed in claim 6 further comprising the step of:
    automatically measuring the resonant frequency and Q factor of the microwave resonator with t an on-line computing device.

11. A process for the measurement of complex permittivity of dielectric materials as claimed in claim 6, wherein the size of the dielectric material under test is selected from the group consisting of:
    (a) smaller than the microwave resonator;
    (b) larger than the microwave resonator;
    (c) of the size of the microwave resonator.

* * * * *